Figure 1:
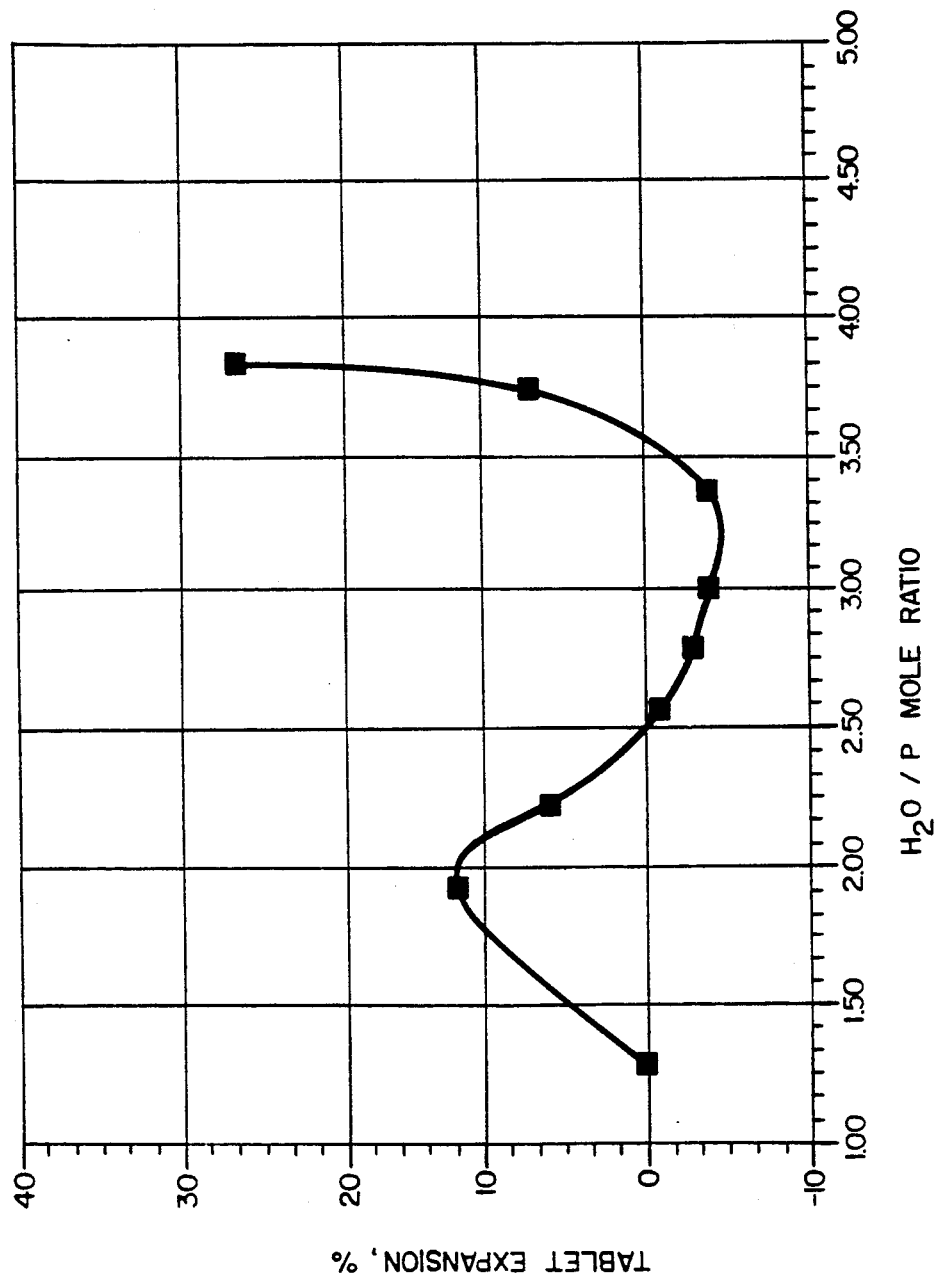

United States Patent [19]

Haddad et al.

[11] Patent Number: 5,134,106
[45] Date of Patent: * Jul. 28, 1992

[54] MALEIC ANHYDRIDE CATALYSTS

[75] Inventors: Muin S. Haddad; William S. Eryman, both of Naperville, Ill.

[73] Assignee: Amoco Corporation, Chicago, Ill.

[*] Notice: The portion of the term of this patent subsequent to Oct. 23, 2007 has been disclaimed.

[21] Appl. No.: 657,487

[22] Filed: Feb. 19, 1991

Related U.S. Application Data

[63] Continuation of Ser. No. 262,743, Oct. 26, 1988, Pat. No. 5,019,545, which is a continuation-in-part of Ser. No. 225,523, Jul. 28, 1988, abandoned.

[51] Int. Cl.$^5$ .................... B01J 27/98; B01J 37/28
[52] U.S. Cl. .................... 502/209; 502/162; 502/211
[58] Field of Search .................. 502/209–213

[56] References Cited

U.S. PATENT DOCUMENTS

| | | | |
|---|---|---|---|
| 3,977,998 | 8/1976 | Freerks et al. | 502/209 |
| 4,396,535 | 8/1983 | Bremer et al. | 502/209 |
| 4,418,003 | 11/1983 | Udovich | 502/209 |
| 4,567,158 | 1/1986 | Wrobleski et al. | 502/209 |
| 4,652,543 | 3/1987 | Edwards et al. | 502/209 |
| 4,699,895 | 10/1987 | Edwards | 502/209 |
| 4,701,433 | 10/1987 | Edwards | 502/209 |
| 4,732,885 | 3/1988 | Edwards et al. | 502/209 |
| 4,784,981 | 11/1988 | Alpers et al. | 502/209 |
| 4,915,904 | 5/1985 | Edwards | 502/209 |
| 4,957,894 | 9/1990 | Haddad et al. | 502/209 |
| 4,965,235 | 10/1990 | Haddad et al. | 502/209 |

Primary Examiner—Paul E. Konopka
Attorney, Agent, or Firm—Rae K. Stuhlmacher; William H. Magidson; Robert J. Wagner

[57] ABSTRACT

Novel maleic anhydride catalysts comprising phosphorus-vanadium oxides and phosphorus-vanadium-cometal oxides which under reaction conditions for the manufacture of maleic anhydride from butane feedstock do not expand to the point of crushing and producing fines.

5 Claims, 1 Drawing Sheet

CATALYST TABLET EXPANSION AS A FUNCTION OF REACTION $H_2O/P$ MOLE RATIO

MALEIC ANHYDRIDE CATALYSTS

This is a continuation of application Ser. No. 262,743, filed Oct. 26, 1988, now U.S. Pat. No. 5,019,545, issued on May 28, 1991 which in turn is a continuation-in-part of Ser. No. 225,523 filed Jul. 28, 1988 now abandoned.

FIELD OF THE INVENTION

The field of this invention relates to novel catalysts and to processes for the manufacture of phosphorus-vanadium mixed oxide and phosphorus-vanadium-co-metal mixed oxide catalysts suitable for the oxidation of benzene, butane, butene, and butadiene to maleic anhydride wherein under oxidation conditions of the hydrocarbon the catalyst particles do not expand.

BACKGROUND

Maleic anhydride is of significant commercial interest throuqhout the world and is extensively used in the manufacture of alkyd resins. It is also a versatile intermediate for chemical synthesis. Consequently, large quantities of maleic anhydride are produced each year to satisfy these needs.

In general, catalysts proposed for the oxidation of butane to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 wt. % are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116: 4,152,338: 4,152,339: 4,403,943; 4,154,703 and British Application 2,019,839A. While the aforementioned prior art tends to bring about some improvement in the performance of the phosphorus-vanadium catalyst, there remains much room for improvement, particularly from the standpoint of high conversion, yield, and catalyst life. Other references of interest include U.S. Pat. Nos. 4,020,174; 4,094,816; 4,089,807: 3,296,282; 3,474,041 and British Patent 1,464,198. All of these references relate to catalyst regeneration and not to catalyst stability.

Also, U.S. Pat. Nos. 3,915,892 and 3,985,775 teach a process for preparing catalysts suitable for preparing maleic anhydride from n-butane comprising a mixed vanadium-phosphorus oxide wherein one of the process steps consists of heating the components to between 350° C. and 410° C. in an oxygen-containing gas. The function of this step is to remove water of hydration from the dihydrate of the mixed oxide of the vanadium and pentavalent phosphorus complex. These patents do not teach the use of air or other oxygen-containing gas in the catalyst reaction step or in the drying step for removing the bulk of the water or other reaction solvents.

Our catalyst is suitably prepared in organic solvents by slurring vanadium compounds and metals or metal oxides such as molybdenum oxide, zinc oxide, uranium oxide, tungsten oxide, tin oxide, bismuth oxide, titanium oxide, niobium oxide, antimony oxide and cobalt oxide in organic solvents, preferably organic ether solvents. A small amount of water or a hydrogen donor compound, such as a lower alcohol, is also present in the ether. Suitable alcohols are ethanol and methanol and suitable ethers are tetrahydrofuran (THF), tetrahydropyran, 1,2-dimethoxyethane, bis(2-methoxyethyl)ether, 1,4 dioxane, ethylether, propylether, butylether, and pentylether. Phosphoryl halide is slowly added to the slurry. The water or hydrogen donor reacts with the phosphoryl halide to generate anhydrous phosphoric acid or phosphate esters and hydrogen halide gas. The hydrogen halide dissolves both the vanadium compound, for example, the vanadium pentoxide, and the co-metal compound and also reduces the vanadium from a valence state of about five to a valence state of about four. This reaction takes places at a temperature of about 0° C. to about 200° C.

While the reaction solution is being refluxed, if desired, a modifier or mixture of modifiers such as o-oxylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid or trimellitic acid, is suitably added to the reaction solvent. After refluxing, the color of the solution is green. The volume of the solution is reduced by distillation or evaporation until it becomes a thick syrup. This syrup is dried at a temperature of about 130° C. to about 200° C. and 0–15 inches of mercury vacuum. Once dry, the color of the solid material is brown. The catalyst can be formed into geometric forms, such as cylinders, using graphite, Sterotex or other lubricants such as stearic acid, zinc stearate or starch and binders such as polyvinyl alcohol. The catalyst in the form of geometric shapes or in powder form is suitably calcined in air or a nitrogen-air combination before loading into a suitable tubular reactor. The catalyst is activated further by the addition of water and phosphorus compounds or mixtures thereof such as alkylphosphates, phosphites, and phosphines. This activation takes place at a temperature of about 300° C. to about 500° C. Representative phosphorus compounds have the following structure:

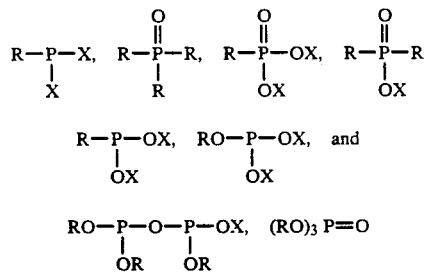

wherein R is phenyl or an alkyl radical of 1 to 6 carbon atoms and X is H or R. Suitable compounds are primary, $RPH_2$, secondary, $R_2PH$, and tertiary, $R_3P$, phosphines, such as ethyl phoshine; the tertiary phosphine oxides, $R_3PO$, such as tripropyl phosphine oxide, the primary, $RP(O)(OX)_2$, and secondary $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(ROR)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1-C_4$ alkyl, at least one R being a $C_1-C_4$ alkyl. The preferred phosphorus compounds are triethylphosphate and trimethylphosphate.

Our novel catalyst for the production of maleic anhydride comprising a phosphorus-vanadium mixed oxide is prepared by a reaction wherein the level of water added to the reaction mixture of phosphorus compound, vanadium compound and, optionally, the co-metal compound is kept within a preferred range. This preferred range for the level of water added is from about 2.25 to about 3.75 moles of water per mole of phosphorus and more preferably from about 2.5 to 3.5 moles of water per mole of phosphorus in the reaction mixture. If either an excess or an insufficient amount of water is added, the catalyst prepared will expand excessively during use. The expanded catalyst is not suitable for continued commercial use because the expansion causes an undesirable pressure drop across the reactor tube containing the catalyst tablets. The excessive pressure drop will not allow for the appropriate flow of reactant and product materials through the reactor tube.

In co-pending application Ser. No. 225,523, which is specifically incorporated by reference, we disclosed the novel phosphorus-vanadium mixed oxide and metal promoted phosphorus-vanadium mixed oxide catalysts and the processes for making these catalysts wherein these catalysts do not expand during the manufacture of maleic anhydride. These catalysts were prepared by using an oxygen containing atmosphere during the reaction step for synthesizing the catalyst, where the total gas blanketing the reaction contains at least 0.1% by weight oxygen. We have now further determined that the level of water used in the reaction to prepare these maleic anhydride catalysts is also a critical factor and that the molar ratio of water to phosphorus must be kept within the range of from about 2.25:1 to about 3.75:1, or more preferably in the range of from about 2.5:1 to about 3.5:1. Therefore in order to prepare a phosphorus-vanadium mixed oxide or metal promoted phosphorus-vanadium mixed oxide catalyst that does not expand during the production of maleic anhydride the catalyst is best prepared in a reaction wherein the molar ratio of water to phosphorus is in the range of about 2.25:1 to about 3.7:1 and preferably in the range of about 2.5:1 to about 3.5:1, respectively, and wherein the reaction is conducted in an atmosphere containing oxygen wherein the atmosphere comprises at least 0.1% wt. % oxygen of the total gas blanketing the reaction. By only controlling the water to phosphorus molar ratios of this invention, catalyst expansion will be reduced, however, superior results are achieved when the control of the water level and the use of an oxygen-containing gas as an atmosphere during the reaction step of preparing the catalyst are both employed.

The novel catalyst comprises a phosphorus-vanadium mixed oxide or a phosphorus-vanadium mixed oxide promoted by metals. The atomic ratio of the vanadium to phosphorus can suitably be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium or cobalt to vanadium should be in the ranqe of 0.001:1 to 0.2:1.

The co-metal, such as molyhdenum, zinc, tungsten, uranium, bismuth, titanium, antimony, niobium, cobalt or tin may be added as a compound together with vanadium, or separately introduced into the solution. Suitable co-metal compounds comprise their oxides and soluble salts. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice or silica. The catalyst may be reinforced with such materials at any stage in its preparation.

According to our process, the average valence of vanadium is in the range of about 3.8 to 4.2. In our catalyst preparation, various phosphoryl halides may be used, but $POCl_3$ is preferred. The catalyst can be activated in the presence of water and:

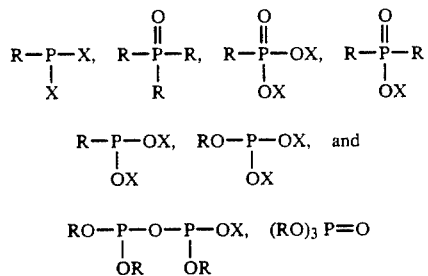

wherein R is phenyl or an alkyl radical of 1 to 6 carbon atoms and X is H or R. Suitable compounds are the primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof such as the monoethyl ester; the phosphinous acids, $R_2POX$, such as diethyl phosphinous acid and the esters thereof, such as the monoethyl ester; the primary, $ROP(OX)_2$, secondary $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1-C_4$ alkyl, at least one R being a $C_1-C_4$ alkyl. The preferred phosphate compounds are triethylphosphate and trimethylphosphate.

The amount of water added is about 1,000 to about 40,000 parts per million of the reaction feed gas stream. The reaction feed gas stream comprises hydrocarbon and air.

Suitable vanadium compounds include: vanadium oxides, such as vanadium pentoxide, vanadium trioxide and the like: vanadium oxyhalides, such as vanadyl chloride, vanadyl dichloride, vanadyl trichloride, vanadyl bromide, vanadyl dibromide, vanadyl tribromide and the like; vanadium-containing acids, such as metavanadic acid, pyrovanadic acid and the like: vanadium salts, such as ammonium meta-vanadate, vanadium sulfate, vanadium phosphate, vanadyl formate, vanadyl oxalate and the like; however, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic mixtures of oxygen and diluent gases, such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about 1%, of course, will reduce the total yield obtained at equivalent flow rates and, thus, are not normally economically employed. The flow rate of the gaseous stream through the reactor may be varied within rather wide limits, but preferred range of operations is at the rate of about 100 to 4,000 cc of feed per cc of catalyst per hour, and more preferably about 1,000 to 2,400 cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 0° C. A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulfur, mercury, molten lead and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature-regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone under an inert material such as one-quarter-inch Alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, superatmospheric, or subatmospheric pressure. The exit pressure will be at least slightly higher than the ambient pressure to ensure a positive flow from the reactor. The pressure of the inert gases must be sufficiently high to overcome the pressure drop through the reactor.

Maleic anhydride is currently produced by fixed bed catalyst oxidation of butane over mixed vanadium oxide catalyst. The catalyst is usually formed into tablets prior to loading in the multitubular reactor. The size and shape of these tablets are important since they determine the void fraction available in the reactor. It is important that this void fraction be large enough to avoid development of a large pressure drop across the reactor. One such suitable tablet is a right cylinder. In addition to its dependence on the shape and dimensions of the tablet, the reactor's void fraction depends on whether those dimensions change under hydrocarbon conversion conditions. For example, if the tablet undergoes a volume increase or "expansion" the void fraction will decrease and an unacceptable increase in pressure drop will result. We discovered that tablets made from calcined catalyst powder underwent an unexpected expansion in a standard expansion test as well as under hydrocarbon conversion conditions in a large pilot plant. This expansion resulted in unacceptably high pressure drop across the catalyst bed. We discovered that this catalyst expansion can be caused by using either an excess or an insufficient amount of water in the catalyst preparation procedure. We discovered that by controlling this amount of water to keep it within a preferred range the catalyst expansion can be prevented.

Maleic anhydride may be recovered by a number of ways well known to those skilled in the art. For example, the recovery may be by direct condensation or by absorption in suitable media, with specific operations and purification of the maleic anhydride. The following examples will serve to provide full understanding of the invention, but it is to be understood that these examples are given for illustrative purposes only and will not be interpreted as limiting the invention in any way.

TYPICAL CATALYST PREPARATION

To a 3-liter, 3-neck, round bottom flask equipped with a thermowell, electrical mantle, mechanical stirrer, and reflux condenser, are added 728 g $V_2O_5$, 34.56 g $MoO_3$, 540 g water, and 2,000 ml tetrahydrofuran (THF). A purge gas of 91 wt. % $N_2$/9 wt. % $O_2$ is established at a rate of 0.8 standard cubic feet per hour. $POCl_3$ (1534 g) is added from an addition funnel over a period of 2 hours. During the $POCl_3$ addition an exothermic reaction occurs which results in a continuous temperature rise, reflux of the solvent and dissolution of the solids. The mixture turns from a yellow orange slurry to red brown solution as the $POCl_3$ addition progresses At the end of $POCl_3$ addition the deep green solution is heated up to reflux and maintained at reflux for 2 hours. The black, green syrup is then dried overnight at about 3 in. of Hg vacuum with a mild air, nitrogen, or N$_2$/air purge passing through the oven. Drying temperature and time vary from 130° C. to 200° C. and 18 to 48 hours respectively.

The dark brown catalyst powder is ground, calcined at 300° C. in air for 4 hours and formed into $\frac{3}{16}$" cylindrical tablets using 5 wt. % graphite as a lubricant. The side crush strength of the tablets is about 5.9 lbs.

Expansion Test

In an expansion test the length and diameter of 10 tablets are measured with a caliper. An average volume is determined using the volume relationship for a cylinder. The tablets are then introduced to an oven at 900° F. The tablets are kept at that temperature in a humid air stream for 2 hours. The tablets are removed from the oven and allowed to cool in a desiccator. The length and diameter of the tablets are measured and an average volume is determined. The comparison of the average volume of the tablet before and after introduction to the oven determines whether the tablets expanded, shrank, or remained the same.

EFFECT OF THE LEVEL OF WATER IN THE CATALYST REACTION STEP ON TABLET EXPANSION

The following examples demonstrate that by keeping the ratio of water to phosphorus in the reaction mixture during the step of catalyst synthesis to within the preferred ranges of this invention the result is a catalyst tablet that does not undergo excessive expansion upon use.

EXAMPLES 1-4

The catalyst of Example 1 in Table 1 was prepared according to the typical catalyst preparation described above. The catalysts of Examples 2-4 were prepared similarly except the mole ratio of water to phosphorus and the mole ratio of water to tetrahydrofuran (THF) were varied as shown in Table 1. These data point out that by reducing the molar ratio of water to phosphorus to below 3.0 in the reaction mixture the resulting catalyst tablet expands in the tablet expansion test. However, reducing the ratio of water to tetrahydrofuran as shown in Example 4 does not result in tablet expansion. These results demonstrate that the water to phosphorus mole ratio is the critical variable for controlling catalyst expansion and not the ratio of water to tetrahydrofuran.

TABLE I

Effect of Water Content in Catalyst Reaction Step on Tablet Expansion

| Example No.[1] | H$_2$O/P mole ratio | H$_2$O/THF mole ratio | Tablet Expansion |
|---|---|---|---|
| 1 | 3 | 1.23 | −4% |
| 2 | 2.22 | 0.9 | +6% |
| 3 | 2.22 | 1.23 | +5% |
| 4 | 3 | 0.9 | −3% |

[1] Example 1 represents the standard preparation.

EXAMPLES 5-13

The catalysts of Examples 5-13 shown in Table II were also prepared according to the typical catalyst preparation described above except that the mole ratio of water to phosphorus during the reaction was varied over the range of 1.28 to 3.83 moles of water per mole of phosphorus. These data clearly demonstrate the sensitivity of the tablet expansion to variation in the water to phosphorus mole ratio. No change in catalyst tablet volume or only a slight tablet shrinkage rather than undesirable expansion occurs only over the limited range of from about 2.6 to about 3.4 moles of water per mole of phosphorus. At very low water to phosphorus mole ratios as shown in Example 5, catalyst expansion is acceptable but the reaction mixture becomes too viscous and may be impractical for commercial use.

EXAMPLE 14

The data from Table II are plotted in FIG. 1 where the relationship of catalyst tablet expansion to the mole ratio of water to phosphorus in the reaction mixture is readily apparent. Based on this plot, a preferred range for the molar ratio of water to phosphorus atoms in the reaction mixture is about 2.25 to about 3.75. Within this range, the prepared catalysts do not expand at all or expand at most only about 5%. More preferably, the molar ratio of water to phosphorus atoms is from about 2.5 to about 3.5. Within this range, the prepared catalysts do not expand at all and, in fact, exhibit a slight decrease in volume in the catalyst tablet expansion test.

TABLE II

Effect of Reaction H$_2$O/P Mole Ratio on Amoco III Tablet Expansion

| Example No. | H$_2$O/P Mole Ratio | Tablet Expansion |
|---|---|---|
| 5 | 1.28 | +0.24 |
| 6 | 1.92 | +11.6 |
| 7 | 2.22 | +6 |
| 8 | 2.56 | −0.9 |
| 9 | 2.78 | −3 |
| 10 | 3.0 | −4 |
| 11 | 3.37 | −4 |
| 12 | 3.74 | +7 |
| 13 | 3.83 | +26.5 |

EXAMPLES 15-18

The data from Examples 15-18 shown in Table III demonstrate further that excessive catalyst tablet expansion is caused by a high ratio of water to phosphorus during the catalyst preparation and that the expansion is significantly reduced if an oxygen-containing atmosphere is used during the catalyst preparation step. The catalysts from Examples 15-18 were all prepared in accordance with the typical catalyst preparation described above except that the mole ratio of water to phosphorus was 3.74, a ratio that causes excessive catalyst expansion. Data for Examples 15 and 16 show that the use of nitrogen, an inert gas, for the reaction atmosphere during catalyst preparation results in an expansion of +33%. In otherwise identical reactions, except that a mixture of oxygen and nitrogen was used for the reaction atmosphere, Examples 17 and 18 show that catalyst expansion was only 7-8%. These data clearly demonstrate the advantageous results obtained by using an oxygen-containing atmosphere during the reaction stage of catalyst preparation. Even when excess water is added to the reaction mixture during the preparation of the maleic anhydride catalyst, which from time to time could inadvertently happen, the use of an oxygen-containing atmosphere during the catalyst preparation reaction will greatly lessen the amount of catalyst tablet expansion that would otherwise occur if an inert gas such as nitrogen were used. Therefore the preferred process for the preparation of the phosphorus-vanadium mixed oxide or phosphorus-vanadium-cometal mixed oxide catalysts for maleic anhydride production of this invention is to use an oxygen-containing gas for the reaction atmosphere during catalyst preparation and to adjust the ratio of water to phosphorus during the reaction to prepare the catalyst to within the ran9e of about 2.25:1 to about 3.75:1 or more preferably from about 2.5:1 to about 3.5:1.

TABLE III

Effect of Reaction Atmosphere on Catalyst Tablet Expansion[1]

| Example No. | Reaction Atmosphere | Drying Atmosphere | Tablet Volume Change, % |
|---|---|---|---|
| 15 | $N_2$ | Air | +33 |
| 16 | $N_2$ | $N_2$ | +33 |
| 17 | $N_2/O_2$ | Air | +7.0 |
| 18 | $N_2/O_2$ | $N_2$ | +7.8 |

[1]$H_2O/P$ Mole Ratio = 3.74

We claim:

1. A catalyst suitable for use in the manufacture of maleic anhydride from butane, benzene, butene or butadiene comprising mixed oxides of phosphorus and vanadium, characterized by a vanadium/phosphorus atomic ratio of 0.5:1.0 to 1.25:1.0 and an average valence state of vandium from about +3.8 to about +4.2, wherein the catalyst does not expand in excess of 5% nor contract in excess of 10% upon use in the production of maleic anhydride, which catalyst is prepared by the steps comprising:
   (a) reacting in a reaction mixture at a temperature of about 0° C. to about 200° C. a vanadium compound in an organic ether solvent with a phosphoryl halide in the presence of water, wherein the molar ratio of water to phosphorus from the phosphoryl halide is in the range of about 2.25:1 to about 3.75:1;
   (b) eliminating the solvent; and
   (c) activating the catalyst by the addition of butane, benzene, butene or butadiene at a temperature of about 300° C. to about 500° C;
wherein an oxygen-containing gas is introduced into said reaction mixture at a rate sufficient to provide an atmosphere comprising at least about 0.1 wt. % oxygen during said reaction.

2. The catalyst of claim 1 wherein a co-metal is used as a promoter wherein the total ratio of the co-metal to vanadium is in the range of about 0.001:1 to about 0.4:1.

3. The catalyst of claim 2 wherein the co-metal is molybdenum.

4. The catalyst of claim 2 wherein the co-metal is zinc.

5. The catalyst of claim 1 wherein the molar ratio of water to phosphorus is in the range of about 2.5:1 to about 3.5:1.

* * * * *

UNITED STATES PATENT AND TRADEMARK OFFICE
CERTIFICATE OF CORRECTION

PATENT NO. : 5,134,106

DATED : July 28, 1992

INVENTOR(S) : Muin S. Haddad, et al

It is certified that error appears in the above-identified patent and that said Letters Patent is hereby corrected as shown below:

| Column | Line | |
|---|---|---|
| 1 | 20 | "throuqhout the world" should read --throughout the world-- |
| 3 | 51 | "to about 3.7:1" should read --to about 3.75:1-- |
| 4 | 2 | "in the ranqe" should read --in the range-- |
| 4 | 4 | "such as molyhbdenum" should read --such as molybdenum-- |
| 8 | 19 | "Within this ranqe" should read --Within this range--. |
| 9 | 6 | "ran9e of about" should read --range of about-- |

Signed and Sealed this

Twenty-first Day of September, 1993

Attest:

BRUCE LEHMAN

Attesting Officer     Commissioner of Patents and Trademarks